United States Patent [19]
Kissener et al.

[11] Patent Number: 5,756,831
[45] Date of Patent: May 26, 1998

[54] PROCESS FOR THE PREPARATION OF 5-FLUORO-2-NITROBENZOIC ACID

[75] Inventors: Wolfram Kissener, Neunkirchen-Seelscheid; Jürgen Kuprat, Wermelskirchen; Herbert Emde, Köln; Klaus-Christian Paetz, Burscheid, all of Germany

[73] Assignee: Bayer Aktiengesellschaft, Leverkusen, Germany

[21] Appl. No.: 667,833

[22] Filed: Jun. 20, 1996

[30] Foreign Application Priority Data

Jun. 27, 1995 [DE] Germany .................. 195 23 244.5

[51] Int. Cl.$^6$ .................................................. C07C 205/58
[52] U.S. Cl. ............................................................. 562/438
[58] Field of Search ............................................... 562/438

[56] References Cited

U.S. PATENT DOCUMENTS 5,543,550  8/1996  Rapp et al. .......................... 562/438

FOREIGN PATENT DOCUMENTS 0 647 615 A1  4/1995  European Pat. Off. .

OTHER PUBLICATIONS

Ege, Liebigs Ann. Chem 1976 pp. 946,960, 1976.

Wiberg, Laboratory Technique in Organic Chemistry p.99, 1960.

J. Farmer et al, Tetrahedron Letters, vol. 29, No. 40, pp. 5105–5108 (1988).

H. Slothouwer, Recueil Des Travaux Chimiques De Pays–Bas, vol. 33, pp. 324–342 (1914).

*Primary Examiner*—Robert Gerstl
*Attorney, Agent, or Firm*—Sprung Kramer Schaefer & Briscoe

[57] ABSTRACT

5-Fluoro-2-nitrobenzoic acid having low contents of 3-fluoro-2-nitro-benzoic acid is prepared in a simple manner by nitrating 3-fluorobenzoic acid in an anhydrous medium using an anhydrous nitrating acid and isolating and purifying 5-fluoro-2nitro-benzoic acid, by taking 7.5 to 15 parts by weight of water, based on 1 part by weight of 3-fluorobenzoic acid used, introducing the reaction mixture reacted to exhaustion into this volume of water taken, filtering off the precipitate formed and washing it with water.

10 Claims, No Drawings

PROCESS FOR THE PREPARATION OF 5-FLUORO-2-NITROBENZOIC ACID

The present invention relates to a process for the preparation of 5-fluoro-2-nitro-benzoic acid in which a product is obtained which contains particularly low amounts of 3-fluoro-2-nitro-benzoic acid. 5-Fluoro-2-nitro-benzoic acid is an important intermediate which is used, after reduction to the corresponding anthranilic acid, for the preparation of pharmaceuticals and agrochemicals (see, for example, U.S. Pat. No. 3,905,880, U.S. Pat. No. 4,388,472, U.S. Pat. No. 4,824,469, EP-A 109 757, EP-A 183 458, French Patent No. 2 541 288 and Czech Patent 159 570). For this purpose, it is highly desirable that the intermediate is available in the purest possible form, in order to be able to prepare the purest possible active compounds therefrom.

According to the prior art (see EP-A 647 615), it is not possible to separate off 3-fluoro-2-nitro-benzoic acid from 5-fluoro-2-nitro-benzoic acid or to separate off its reduction product 3-fluoroanthranilic acid from 5-fluoroanthranilic acid. The said EP-A therefore proposes nitrating not 3-fluorobenzoic acid, but 3-fluorobenzoic ester and separating off, by distillation or melt crystallization, either 3-fluoro-2-nitro-benzoic ester from 5-fluoro-2-nitro-benzoic ester or, after reduction thereof, 3-fluoroanthranilic ester from 5-fluoroanthranilic ester.

In order to have 5-fluoroanthranilic acid available for the preparation of active compounds, the ester must then be resaponified. This process requires high expenditure, since it includes in each case the stages of esterification, isomer separation by distillation or melt crystallization and ester saponification.

There was therefore the requirement for a less complex process by which the purest possible 5-fluoro-2-nitro-benzoic acid can be obtained.

A process has now been found for the preparation of 5-fluoro-2-nitro-benzoic acid by nitration of 3-fluorobenzoic acid, which is characterized in that the nitration is carried out in an anhydrous medium using an anhydrous nitrating acid and 5-fluoro-2-nitro-benzoic acid is isolated and purified, by taking 7.5 to 15 parts by weight of water, based on one part by weight of 3-fluorobenzoic acid used, introducing the reaction mixture reacted to exhaustion into this volume of water, filtering off the precipitate formed and washing it with water.

The anhydrous medium used for the nitration can be e.g. 100% strength by weight of sulphuric acid. Per 1 part by weight of 3-fluorobenzoic acid, for example, 2.5 to 8, preferably 3 to 5, parts by weight of 100% strength by weight sulphuric acid can be used.

As anhydrous nitrating acid, use can be made of e.g. anhydrous nitric acid and any mixtures of 100% strength by weight sulphuric acid and 100% strength by weight nitric acid. The said mixtures are preferred and can contain e.g. 20 to 90% by weight sulphuric acid and nitric acid to make up 100% by weight. Preferably, mixtures of this type contain 50 to 80% by weight sulphuric acid and nitric acid to make up 100% by weight. The amount of the nitrating acid is expediently such that, per mole of 3-fluorobenzoic acid, 1 mol or more of nitric acid is used. Preferably, the amount of nitric acid is 1 to 1.5 mol per mol of 3-fluorobenzoic acid.

If, for the preparation of anhydrous nitrating acid, no completely anhydrous nitric acid is available, an anhydrous nitrating acid can be obtained by using, instead of anhydrous sulphuric acid, oleum or a mixture of oleum and sulphuric acid. Then, expediently, the concentration or quantity of oleum used is such that the sulphur trioxide present therein is equivalent in molar terms to the water content of the nitric acid.

The nitration can be carried out, e.g. in the temperature range −10 to +35° C. Preferably, it is carried out at −5 to +15° C.

After the nitration is completed, a reaction mixture is generally obtained which contains 1 to 2% by weight 3-fluoro-2-nitro-benzoic acid, based on 5-fluoro-2nitro-benzoic acid. At a relatively high nitration temperature, e.g. at +10 to +35° C., the reaction mixture contains e.g. 1.5 to 2.0% by weight 3-fluoro-2-nitro-benzoic acid, based on 5-fluoro-2-nitro-benzoic acid, and at a relatively low nitration temperature, e.g. at −10 to +5° C., only e.g. 1.0 to 1.5% by weight. At all events, the reaction time is then longer.

A particular embodiment of the nitration of the invention is characterized in that the reaction mixture, at the start of the nitration, additionally contains dehydrating agents. These can be, for example, sulphur trioxide, oleum or phosphorus pentoxide or a mixture of sulphuric acid, phosphoric acid and phosphorus pentoxide. The dehydrating agents can be added e.g. to the anhydrous nitrating medium and/or the anhydrous nitrating acid. In this embodiment of the nitration of the invention, reaction water formed during the nitration is chemically bound. For example, dehydrating agents can be used in a quantity which is able to bind 10 to 150% by weight of the reaction water released. Preferably, the amount of dehydrating agents used is that required to bind 90 to 110% by weight of the reaction water released.

When operations are carried out in accordance with this embodiment, after completion of the nitration, reaction mixtures are generally obtained which, based on 5-fluoro-2-nitro-benzoic acid, contain 0.1 to 0.5% by weight less 3-fluoro-2nitro-benzoic acid than when the nitration is carried out in the absence of dehydrating agents.

After completion of the nitration, 7.5 to 15 parts by weight, preferably 8 to 12 parts by weight, based on one part by weight of 3-fluoro-benzoic acid used, are taken and the reaction mixture reacted to exhaustion is introduced into this water. It is advantageous in this case to keep the temperature of the mixture e.g. in the range 0 to +100° C., preferably in the range +30 to +80° C. The water taken can contain e.g. fresh water, ice and/or recycled washing water. The precipitate formed is filtered off, e.g. at a temperature in the range 10 to 50° C.

Finally, the precipitate filtered off is washed with water. This frees it from adhering acid and substantially leaches out 3-fluoro-2-nitro-benzoic acid still present. Since not only 3-fluoro-2-nitro-benzoic acid, but also 5-fluoro-2-nitro-benzoic acid, dissolves in the washing water, it is expedient to determine by simple preliminary experiments the amount of total washing water optimal for the given individual case. In this case the following applies; 5-fluoro-2-nitro-benzoic acid is obtained with increasing purity and decreasing yield if larger amounts of washing water are used.

Generally, satisfactory results are obtained if, in total, 5 to 10, preferably 6 to 9, parts by weight of washing water are used, based on 1 part by weight of 3-fluoro-benzoic acid used. It is advantageous to arrange this washing to be multistage, e.g. 2 to 5-stage, identical or different amounts of washing water being able to be used in the individual stages.

Advantageously the washing water is recirculated, i.e. it is used to prepare the volume of water taken into which the nitrating mixture reacted to exhaustion is introduced.

The process of the invention permits the preparation of 5-fluoro-2-nitro-benzoic acid with contents of 3-fluoro-2-nitro-benzoic acid of generally less than 0.4% by weight, frequently less than 0.2% by weight, where, for purification, in contrast to the prior art, no conversion into another compound class (ester instead of acid) and no complex separation operations (such as distillation or melt crystallization) are necessary.

The process of the invention gives 5-fluoro-2-nitrobenzoic acid in yields of generally greater than 85% of theory. When the washing water is recycled into the amount of water taken into which the nitration mixture reacted to exhaustion is introduced, yields generally greater than 90% of theory are achieved.

EXAMPLES

The percentages by weight of wrong isomers are always based on 5-fluoro-2-nitro-benzoic acid present. Wrong isomers are essentially 3-fluoro-2-nitro-benzoic acid.

Example 1

841 g of 3-fluorobenzoic acid were placed in 3261 g of 100% strength by weight sulphuric acid and the mixture was cooled to +10° C. 1147 g of nitrating acid comprising 67% by weight of 100% strength by weight sulphuric acid and 33% by weight of 100% strength by weight nitric acid were then added. After the reaction was completed, the mixture contained approximately 1.65% by weight of wrong isomers. The mixture was added to 10 l of water and then cooled to room temperature. The solid product precipitated out was filtered off and then washed 3 times, each time with 2 l of water, and dried. 957.8 g of 5-fluoro-2-nitro-benzoic acid (calculated as 100% pure product) were obtained, which corresponds to 86.3% of theory. The product contained 0.17% by weight of 3-fluoro-2-nitro-benzoic acid.

Example 2

The procedure was followed as in Example 1, but the nitration was carried out at different temperatures and the nitration mixture was not further worked up.
a) At a nitration temperature of +25° C., the mixture contained approximately 1.95% by weight of wrong isomers.
b) At a nitration temperature of −5° C., the mixture contained approximately 1.05% by weight of wrong isomers.

Example 3

The procedure was followed as in Example 1, but the nitration was carried out in the presence of dehydrating agents and the nitration mixture was not further worked up.
a) With addition of the amount of $SO_3$ theoretically required to bind the reaction water, the mixture contained approximately 1.45% by weight of wrong isomers.
b) With addition of the amount of $P_2O_5$ theoretically required to bind the reaction water, the mixture contained approximately 1.2% by weight of wrong isomers.

Example 4

The procedure was followed as in Example 1, but the process was carried out at −5° C. and the amount of $SO_3$ theoretically required to bind the reaction water was added. After the reaction was completed, the mixture contained approximately 0.8% of wrong isomers.

What is claimed is:

1. A process for the preparation of 5-fluoro-2-nitrobenzoic acid having a content of 3-fluoro-2-nitrobenzoic acid of less than 0.4% by weight by nitration of 3-fluorobenzoic acid, in which the nitration is carried out in an anhydrous medium using an anhydrous nitrating acid and then the reaction mixtures, reacted to exhaustion, is introduced into 7.5 to 15 parts by weight of water, based on one part by weight of 3-fluorobenzoic acid used, to form a precipitate of 5-fluoro-2-nitrobenzoic acid, the precipitate is then filtered of and washed with water.

2. The process of claim 1, in which the anhydrous medium used is 100% strength by weight of sulphuric acid and the anhydrous nitrating acid used is any mixture of 100% strength by weight sulphuric acid and 100% strength by weight nitric acid.

3. The process of claim 1, in which a nitrating acid is used which contains 20 to 90% by weight of 100% strength sulphuric acid and 100% strength nitric acid to make up 100% by weight.

4. The process of claim 1, in which the amount of nitrating acid used is such that the nitric acid contained therein is 1 to 1.5 mol per mole of 3-fluorobenzoic acid.

5. The process of claim 1, in which the nitration is carried out at temperatures in the range −10 to +35° C.

6. The process of claim 1, in which the nitration is carried out in the additional presence of dehydrating agents.

7. The process of claim 1, in which, per 1 part by weight of 3-fluorobenzoic acid used, 8 to 12 parts by weight of water are taken and, when the reaction mixture reacted to exhaustion is introduced into the volume of water taken, the temperature is kept in the range 0° to +100° C.

8. The process of claim 1, in which the filtration is carried out at a temperature in the range +10° to +50° C.

9. The process of claim 1, in which, for the washing water, in total 5 to 10 parts by weight of washing water are used per 1 part by weight of 3-fluorobenzoic acid used and the washing is arranged to be multistage.

10. The process of claim 1, in which the washing water is recycled into the volume taken into which the reaction mixture reacted to exhaustion is introduced.

* * * * *